(12) United States Patent
Harano et al.

(10) Patent No.: US 12,740,881 B2
(45) Date of Patent: Sep. 22, 2026

(54) LIPOLYSIS DEVICE, LIPOLYSIS METHOD, AND ELECTRIC POWER GENERATION METHOD

(71) Applicant: Murata Manufacturing Co., Ltd., Nagaokakyo (JP)

(72) Inventors: Hiroyuki Harano, Nagaokakyo (JP); Hideyuki Kumita, Nagaokakyo (JP); Yuji Kintaka, Nagaokakyo (JP); Fumiko Mori, Nagaokakyo (JP); Nobuhiko Tanaka, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 507 days.

(21) Appl. No.: 18/457,542

(22) Filed: Aug. 29, 2023

(65) Prior Publication Data

US 2023/0398008 A1 Dec. 14, 2023

Related U.S. Application Data

(63) Continuation of application No. PCT/JP2022/013596, filed on Mar. 23, 2022.

(30) Foreign Application Priority Data

Apr. 30, 2021 (JP) ................................. 2021-077660

(51) Int. Cl.
*H01M 8/16* (2006.01)
*A61F 5/00* (2006.01)
(Continued)

(52) U.S. Cl.
CPC ....... *A61F 5/0013* (2013.01); *A61M 37/0015* (2013.01); *C12N 9/0006* (2013.01);
(Continued)

(58) Field of Classification Search
CPC .............................. H01M 4/9008; H01M 8/16
See application file for complete search history.

(56) References Cited

U.S. PATENT DOCUMENTS

2004/0091757 A1 5/2004 Wang et al.
2014/0024102 A1 1/2014 Sakai et al.

FOREIGN PATENT DOCUMENTS

JP 2006147472 A 6/2006
JP 2011193992 A 10/2011
(Continued)

OTHER PUBLICATIONS

International Search Report in PCT/JP2022/013596, mailed May 31, 2022, 3 pages.

*Primary Examiner* — Kevin E Yoon
(74) *Attorney, Agent, or Firm* — ArentFox Schiff LLP

(57) ABSTRACT

A lipolysis device that includes: a base material having a first surface and a second surface opposite the first surface; a glycerol introduction portion on the first surface of the base material, the glycerol introduction portion having a protrusion containing a lipolytic enzyme or a peptide compound having equivalent activity to that of the lipolytic enzyme; and a glycerol oxidation portion on the second surface of the base material, the glycerol oxidation portion containing glycerol oxidase that oxidizes glycerol introduced from the glycerol introduction portion.

19 Claims, 4 Drawing Sheets

(51) Int. Cl.
*A61M 37/00* (2006.01)
*C12N 9/04* (2006.01)
*H01M 4/90* (2006.01)
*H01M 4/02* (2006.01)

(52) U.S. Cl.
CPC ........... *H01M 4/9008* (2013.01); *H01M 8/16* (2013.01); *A61F 2005/0023* (2013.01); *A61M 2037/0046* (2013.01); *C12Y 101/03021* (2013.01); *H01M 2004/021* (2013.01)

(56) References Cited

FOREIGN PATENT DOCUMENTS

| | | | | | |
|---|---|---|---|---|---|
| JP | 2012190787 | A | | 10/2012 | |
| KR | 101806074 | B1 | * | 12/2017 | ........... A61K 31/165 |
| KR | 20190103903 | A | * | 9/2019 | ........... A61K 9/0021 |

* cited by examiner 1
12 11 10 13
7
9
8
6
4
2
5
3
14
15

LIPOLYSIS DEVICE, LIPOLYSIS METHOD, AND ELECTRIC POWER GENERATION METHOD

CROSS REFERENCE TO RELATED APPLICATIONS

The present application is a continuation of International application No. PCT/JP2022/013596, filed Mar. 23, 2022, which claims priority to Japanese Patent Application No. 2021-077660, filed Apr. 30, 2021, the entire contents of each of which are incorporated herein by reference.

TECHNICAL FIELD

The present invention relates to a lipolysis device, a lipolysis method, and an electric power generation method.

BACKGROUND ART

In recent years, the number of obese people has been rapidly increasing in Japan as well due to changes in the social environment surrounding dietary habits, namely, westernization of dietary habits and lack of exercise. Obesity leads to various diseases, such as lifestyle-related diseases, and beauty problems. Therefore, effective prevention and improvement methods have been required, and research on anti-obesity has been actively conducted.

Here, with growing interest in energy issues in recent years, biofuel cells that use bio-related substances such as sugars and alcohols as fuels have been attracting attention. A biofuel cell uses a biocatalyst as an electrode catalyst, and can generate electric power by combining an oxidation reaction of a biofuel at an anode with a reduction reaction of oxygen or the like at a cathode.

Regarding such a biofuel cell, for example, Patent Document 1 discloses an energy generator that includes conductive reactor gel having an enzyme that decomposes sugar and/or fat and/or fatty acid; a surface electrode arranged in contact with a surface of the reactor gel; and a secondary battery or electric equipment electrically connected to the surface electrode and the reactor gel; and in which the reactor gel takes in the sugar and/or fat and/or fatty acid from a living body when arranged in direct contact with a surface of the living body, and decomposes these living-body-derived components by the enzyme contained in the gel, and the secondary battery is charged or the electric equipment is driven by electric energy generated in the decomposition reaction by the enzyme.

Patent Document 1: Japanese Unexamined Patent Application Publication No. 2006-147472

SUMMARY OF THE INVENTION

However, Patent Document 1 does not disclose any specific means for extracting living-body-derived substances such as sugar and fat in living bodies or specific means for generating energy from recovered living-body-derived substances, and it has been necessary to develop specific means for realizing these.

Further, from the viewpoint of disease prevention, health maintenance, and beauty, it has also been desired to develop a technique for promoting decomposition of fat in living bodies.

The present invention has been made in view of the above-mentioned circumstances and an object of the present invention is to provide a lipolysis device, a lipolysis method, and an electric power generation method, with which energy can be obtained by decomposing fat in living bodies and utilizing glycerol that is an obtained decomposition product.

A lipolysis device according to the present invention includes: a base material having a first surface and a second surface opposite the first surface; a glycerol introduction portion on the first surface of the base material, the glycerol introduction portion having a protrusion containing a lipolytic enzyme or a peptide compound having equivalent activity to that of the lipolytic enzyme; and a glycerol oxidation portion on the second surface of the base material, the glycerol oxidation portion containing glycerol oxidase that oxidizes glycerol introduced from the glycerol introduction portion.

A lipolysis method according to the present invention is a lipolysis method for decomposing fat in a living body and includes: using a lipolysis device that includes a base material having a first surface and a second surface opposite the first surface; a glycerol introduction portion on the first surface of the base material, the glycerol introduction portion having a protrusion containing a lipolytic enzyme or a peptide compound having equivalent activity to that of the lipolytic enzyme; and a glycerol oxidation portion on the second surface of the base material, the glycerol oxidation portion containing glycerol oxidase to prick the living body with the protrusion containing the lipolytic enzyme or the peptide compound having equivalent activity to that of the lipolytic enzyme so as to decompose fat in the living body and obtain glycerol; and oxidizing the glycerol with glycerol oxidase in a glycerol oxidation portion.

An electric power generation method according to the present invention is the electric power generation method for generating electric power using fat in a living body as fuel and includes: pricking the living body with a protrusion, which contains lipolytic enzyme or a peptide compound having equivalent activity to that of the lipolytic enzyme so as to decompose fat in the living body and obtain glycerol; and oxidizing the glycerol in an anode containing glycerol oxidase, and reducing oxygen in air in a cathode.

According to the present invention, a lipolysis device, a lipolysis method, and an electric power generation method, with which energy can be obtained by decomposing fat in living bodies and utilizing glycerol that is an obtained decomposition product, can be provided.

DETAILED DESCRIPTION OF THE PREFERRED EMBODIMENTS

Figures 1, 2:
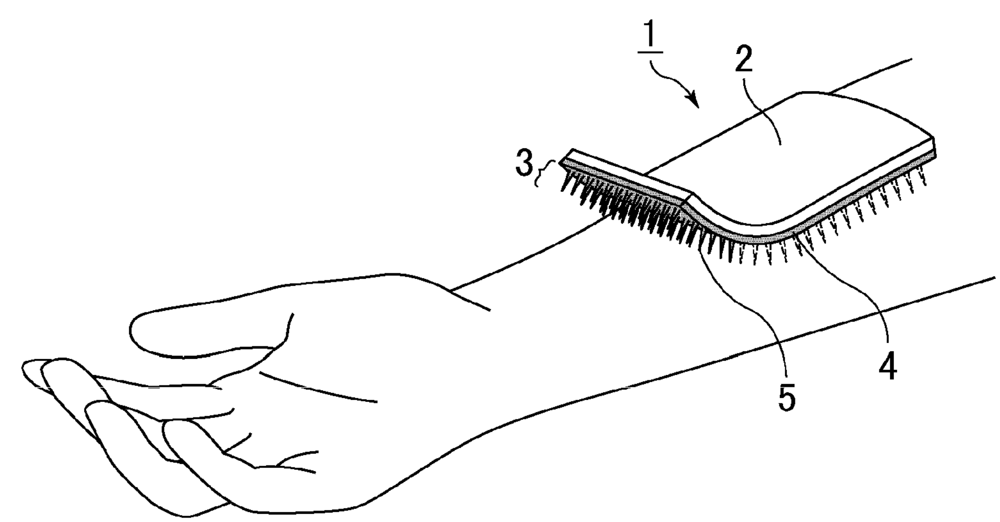
FIG. 1 is a diagram illustrating an example of a lipolysis device, which is in use, according to the present invention.
FIG. 2 is a schematic sectional view of a lipolysis device and skin tissue when the lipolysis device according to the present invention is used.

A lipolysis device, a lipolysis method, and an electric power generation method according to the present invention will be described below.

However, the present invention is not limited to the following configurations and can be appropriately modified and applied without changing the gist of the present invention. A combination of two or more of the individual preferred configurations of the invention described below is also the present invention.

[Lipolysis Device]

A lipolysis device according to the present invention includes a base material having a first surface and a second surface opposite the first surface; a glycerol introduction portion on the first surface of the base material; and a glycerol oxidation portion on the second surface of the base material. In the lipolysis device, the glycerol introduction portion has protrusions containing lipolytic enzyme or peptide compound having equivalent activity to that of lipolytic enzyme (hereinafter also referred to as lipolytic enzyme or the like), and the glycerol oxidation portion contains glycerol oxidase and oxidizes glycerol introduced from the glycerol introduction portion.

A mechanism of energy generation in the lipolysis device according to the present invention is as follows.

When the protrusions of the glycerol introduction portion in the lipolysis device according to the present invention are brought into close contact with a skin and inserted into the skin, lipolytic enzyme or the like is released in skin tissue and subcutaneous fat is decomposed by the lipolytic enzyme or the like. When the fat is decomposed, the concentration of glycerol in body fluids such as interstitial fluid in the skin tissue increases. The glycerol is liquid in living bodies because a melting point of glycerol is 20° C., and the glycerol reaches the glycerol oxidation portion through the protrusions by diffusion. The glycerol that reaches the glycerol oxidation portion is oxidized by oxidase to generate energy.

When this oxidation reaction continues, the concentration of glycerol in body fluids is decreased, accelerating the reaction of fat decomposition into glycerol and fatty acids.

The lipolysis device according to the present invention is capable of generating energy by utilizing fat in living bodies and therefore, a slimming effect by lipolysis can also be expected.

The lipolysis device according to the present invention utilizes fat in living bodies. When fat is decomposed, glycerol and fatty acids are produced. Therefore, it is also conceivable to use fatty acids as substrates. Fatty acids are decomposed to acyl CoA in living bodies by a plurality of enzymes and then oxidized in the β circuit to generate energy. However, in order to extract energy from fatty acids, the fatty acids need to be decomposed by using a plurality of enzymes, making design of the glycerol oxidation portion very complicated. It is thus difficult to artificially reproduce the system of extracting energy from fatty acids. On the other hand, when glycerol is a substrate, energy can be extracted through oxidation by a single enzyme, being able to simplify the configuration of the lipolysis device.

The lipolysis device according to the present invention has protrusions containing a lipolytic enzyme or the like in the glycerol introduction portion. By inserting the protrusions into a skin, the lipolytic enzyme or the like can be released into a living body so as to collect glycerol, which is obtained by fat decomposition, through the protrusions.

The configuration of the protrusions in the glycerol introduction portion is not particularly limited as long as the protrusions contain the lipolytic enzyme or the like and are able to introduce glycerol, which is obtained by fat decomposition, from skin tissue to the glycerol oxidation portion by diffusion or the like. However, the protrusions are preferably porous bodies and/or hollow bodies. More preferably, the protrusions are porous bodies. When the protrusions are porous bodies, in addition to diffusion based on concentration gradient of glycerol in bodily fluids, glycerol can be introduced into the battery portion by a capillary force of the porous bodies as described later. Efficiency of glycerol introduction is thus improved. Further, since the protrusions are porous bodies, adsorption of the lipolytic enzyme or the like to the protrusions is also improved.

When the protrusions are porous bodies, D50 in pore diameter distribution is preferably from 0.05 μm to 10 μm inclusive. This further improves efficiency of introducing glycerol to the battery portion. More preferably, D50 in the pore diameter distribution is from 0.5 μm to 5 μm inclusive. D50 in the pore size distribution can be obtained from a pore diameter distribution curve [horizontal axis: pore diameter (μm), vertical axis: log differential pore volume (mL/g)] measured by mercury porosimetry.

The surfaces of the protrusions are preferably hydrophilic. When the surfaces of the protrusions are highly hydrophilic, affinity for highly hydrophilic glycerol further rises and the efficiency of introducing glycerol to the glycerol oxidation portion is further improved.

Furthermore, when the protrusions are porous bodies and their surfaces are highly hydrophilic, in addition to diffusion based on the concentration gradient of glycerol in bodily fluids, glycerol having a higher hydrophilic property than fatty acids can be selectively introduced into the glycerol oxidation portion by the capillary force of the porous bodies. Accordingly, the efficiency of glycerol introduction is further improved. In addition, when the lipolysis device according to the present invention further includes a battery portion that includes an anode and a cathode connected with the anode, glycerol concentration near the anode is increased and a current value is accordingly increased, and output is improved.

Examples of a method for making the surfaces of the protrusions hydrophilic include a method for imparting hydroxyl groups to the surfaces of the protrusions by using plasma or the like.

It is preferable that a contact angle with water on the surfaces of the protrusions in the lipolysis device is 60° or smaller. This makes the hydrophilic property of the protrusions more sufficient. The contact angle is more preferably 50° or smaller, further more preferably 40° or smaller, and especially preferably 30° or smaller.

The contact angle can be measured with a contact angle meter.

A shape of the protrusion is not particularly limited as long as a skin can be pricked with the protrusion having the shape, but the shape is preferably conical or pyramidal. More preferably, the shape is conical.

The material of the protrusion is preferably a polymer, metal, resin, or the like that does not harm living bodies and is compatible with the living bodies. Specific examples of the material for the protrusion include alginate, hyaluronic acid, curdlan, chitin, chitosan, glucomannan, polymalic acid, collagen, collagen peptide, hydroxypropyl cellulose, gelatin, silicon, titanium, silicone, polylactic acid (PLA), polyglycolic acid (PLA), and PLA-PGA copolymers, and plasma-treated materials of these. Among these, biodegradable materials are more preferable, hyaluronic acid, collagen, and polylactic acid are further more preferable, and polylactic acid is especially preferable.

A length of the protrusion is not particularly limited as long as a skin can be pricked with the protrusion having the length, but the length is preferably from 100 μm to 3000 μm inclusive. This allows lipolytic enzyme or the like to be more sufficiently diffused into subcutaneous fat in a less invasive manner. The length of the protrusion is more preferably from 150 μm to 1500 μm inclusive, further more preferably from 150 μm to 1000 μm inclusive, and especially preferably from 200 μm to 800 μm inclusive.

A diameter of a bottom portion of the protrusion (the maximum diameter of the protrusion) is preferably from 50 μm to 1000 μm inclusive. This makes it possible to prick a skin in a less invasive manner. The diameter of the bottom portion of the protrusion is more preferably from 100 μm to 800 μm inclusive.

The number of protrusions included in the glycerol introduction portion is not particularly limited, but the number is preferably from 25 to 250000 inclusive. More preferably, the number is from 2500 to 50000 inclusive.

The density of protrusions included in the glycerol introduction portion is not particularly limited, but the density is preferably from $1/cm^2$ to $10000/cm^2$ inclusive. More preferably, the density is from $100/cm^2$ to $2000/cm^2$ inclusive.

The method for manufacturing protrusions in the glycerol introduction portion is not particularly limited, and examples of the method include a method for injection-molding a material for forming the protrusions.

The protrusions may be dry or contain a liquid such as a buffer solution. When the protrusions are dry, it is preferable that the inside of the protrusions is under negative pressure, more preferably a vacuum, in a state that the protrusions are covered with a sealing member which will be described later.

The lipolytic enzyme or a peptide compound having equivalent activity to the lipolytic enzyme contained in the protrusions is not particularly limited as long as the lipolytic enzyme or peptide compound is capable of decomposing fat into glycerol and fatty acids. Specific examples of the lipolytic enzyme include lipase and analogues of lipase. The enzyme activity of the peptide compound is preferably from 50 to 120 inclusive when the enzyme activity of lipase is 100. A preferable example of the lipolytic enzyme or the like is lipase or analogues of lipase.

Analogues of the lipolytic enzyme are not particularly limited as long as the analogues of the lipolytic enzyme can decompose fat into glycerol and fatty acids. Examples of the analogues include chemically modified lipase. Examples of the chemically modified lipase include lipase bound with, for example, cell membrane permeable peptide or the like.

An average molecular weight of the lipolytic enzyme or the like is preferably from 2000 to 100000 inclusive. This improves permeability of lipolytic enzyme or the like to fat cells. The average molecular weight is preferably from 5000 to 80000 inclusive, and more preferably from 10000 to 70000 inclusive.

The average molecular weight of the lipolytic enzyme or the like can be measured by ultracentrifugal analysis.

The aspect in which the protrusions contain lipolytic enzyme or the like is not particularly limited, but the lipolytic enzyme or the like is preferably bound to or adsorbed on the protrusions. The above-mentioned binding means chemical bonding and adsorbing means physical adsorption. Examples of the aspect in which lipolytic enzyme or the like is chemically bound to the protrusions include an aspect in which a functional group possessed by lipolytic enzyme or the like and a functional group possessed by the protrusions are bound by ionic bonding.

Examples of the aspect in which the lipolytic enzyme or the like is physically adsorbed on the protrusions include an aspect in which lipolytic enzyme or the like and molecules forming the protrusions are bound by van der Waals forces.

An aspect in which the lipolytic enzyme or the like is physically adsorbed on the protrusions is preferable.

Further, lipolytic enzyme or the like may be directly bound to or adsorbed on the protrusions, but micro-capsules or the like containing the lipolytic enzyme or the like may be bound to or adsorbed on the protrusions.

The method for binding or adsorbing lipolytic enzyme or the like on the protrusions is not particularly limited, but examples of the method include a method in which after the protrusions are immersed in an aqueous solution containing pH-adjusted lipolytic enzyme or the like for a certain period of time, the protrusions are dried at a temperature from 20° C. to 40° C. inclusive.

Further, when the lipolytic enzyme or the like has heat resistance as, for example, lipase derived from highly thermophilic bacteria, the lipolytic enzyme or the like can be embedded in the protrusions in molding of the protrusions by injection molding or the like. For example, when lipolytic enzyme or the like is embedded in protrusions made of a biodegradable material, part of the protrusions are decomposed in a living body after insertion of the protrusions into the living body and accordingly, the lipolytic enzyme or the like can be released in the living body.

The base material is not particularly limited as long as the base material supports the protrusions of the glycerol introduction portion. The base material may be made of the same material as or a different material from that of the protrusions, but the same material is preferable.

The thickness of the base material is preferably from 100 μm to 1000 μm inclusive. More preferably, the thickness is from 300 μm to 500 μm inclusive.

The base material preferably includes an adhesive layer on a portion, on which the protrusions are not formed, of the surface of the base material on the side having the protrusions. This allows a skin and the lipolysis device of the present invention to adhere to each other.

In a state before the use of the lipolysis device according to the present invention, the protrusions in the glycerol introduction portion and the surface of the base material on the side having the protrusions or the adhesive layer are preferably covered by a sealing member. When the protrusions and the surface of the base material on the side having the protrusions or the adhesive layer are covered by a sealing member, the protrusions are exposed by removing the sealing member and the protrusions are accordingly ready to be inserted into a skin.

The glycerol oxidation portion in the lipolysis device according to the present invention is provided on the surface of the base material on the side opposite to the side having the protrusions.

The glycerol oxidation portion is not particularly limited as long as the glycerol oxidation portion contains glycerol oxidase and oxidizes glycerol introduced from the glycerol introduction portion.

The glycerol oxidase is not particularly limited as long as the glycerol oxidase can oxidize glycerol and extract electrons, and analogues of glycerol oxidase may also be employed. The glycerol oxidase is preferably glycerol dehydrogenase, alcohol dehydrogenase, glycerol oxidase, or the like, and more preferably glycerol dehydrogenase or analogues of glycerol dehydrogenase.

When glycerol dehydrogenase, for example, is used as the glycerol oxidase, glycerol is dehydrogenated (oxidized) to produce dihydroxyacetone. Further, when alcohol dehydrogenase is used, glycerol is dehydrogenated (oxidized) to produce glyceraldehyde.

It is preferable that the lipolysis device further includes a suction mechanism that sucks glycerol from the glycerol introduction portion into the glycerol oxidation portion. This further increases an introduction speed of glycerol into the glycerol oxidation portion and allows the glycerol oxidation portion to start glycerol oxidation at an earlier stage.

The suction mechanism is not particularly limited as long as the suction mechanism sucks glycerol into the glycerol oxidation portion from the glycerol introduction portion. Examples of the suction mechanism include a mechanism that utilizes a pressure difference in the lipolysis device and a mechanism that utilizes a capillary force.

When the suction mechanism is the mechanism that utilizes a pressure difference in the lipolysis device, for example, an aspect is employed that the insides of the base material, glycerol oxidation portion, and glycerol introduction portion are in a negative pressure and dry state; a buffer layer containing moisture such as a buffer solution is provided between the base material and the glycerol oxidation portion; and the base material and the buffer layer, and the glycerol oxidation portion and the buffer layer are partitioned by respective partitioning members which are removable or partitioning members which can be broken by external pressure. In this aspect, if the partitioning members are removed or the partitioning members are broken by external pressure, liquid in the buffer layer infiltrates into the base material, glycerol introduction portion, and glycerol oxidation portion and water evaporates from the surface of the glycerol oxidation portion. As a result, the pressure in the glycerol oxidation portion drops below the pressure in the glycerol introduction portion and body fluid in a living body, and this pressure difference allows glycerol in the living body to be sucked through the glycerol introduction portion into the glycerol oxidation portion.

When the suction mechanism is the mechanism that utilizes the capillary force, an aspect that the protrusions in the glycerol introduction portion are porous bodies is employed. Body fluid containing glycerol in a living body is absorbed into pores of porous bodies by the capillary force, allowing glycerol to be sucked into the glycerol oxidation portion.

The lipolysis device preferably includes a battery portion that includes an anode and a cathode connected with the anode, and in this configuration, the anode is the glycerol oxidation portion.

When the lipolysis device includes the battery portion, glycerol produced in skin tissue reaches the anode of the battery portion from the glycerol introduction portion. The glycerol that reaches the anode is oxidized by oxidase and oxygen in the air is reduced at the cathode, generating electric energy.

The lipolysis device according to the present invention including the battery portion can also be referred to as a power generation device.

In the battery portion, an anode is preferably connected to a surface of the base material on a side opposite to the side having the protrusions in the glycerol introduction portion. This allows glycerol, which is introduced into the battery portion through the protrusions, to be more efficiently oxidized in the anode.

The lipolysis device according to the present invention may include a buffer layer between the glycerol introduction portion and the battery portion as described later. In this configuration, the glycerol introduction portion and the anode may be connected via the buffer layer in the use of the lipolysis device according to the present invention.

The anode in the battery portion only needs to contain glycerol oxidase, but glycerol oxidase is preferably immobilized on the surface of the anode.

The anode may further contain a coenzyme oxidase and an electron mediator.

The coenzyme oxidase oxidizes coenzyme (for example, $NAD^+$ and $NADP^+$) that is reduced by oxidase and a reduce form of coenzyme (for example, NADH and NADPH), and examples of the coenzyme oxidase include diaphorase. The action of the coenzyme oxidase produces electrons when the coenzyme reverts to its oxidized form, and the electrons are transferred from the coenzyme oxidase to an electrode via the electron mediator.

A compound having a quinone skeleton is preferably used as the electron mediator, and a compound having a naphthoquinone skeleton is particularly preferred. Specifically, 2-amino-1,4-naphthoquinone (ANQ), 2-amino-3-methyl-1,4-naphthoquinone (AMNQ), 2-methyl-1,4-naphthoquinone (VK3), 2-amino-3-carboxy-1,4-naphthoquinone (ACNQ), and the like can be used.

In addition to the compound having the naphthoquinone skeleton, for example, compounds having an anthraquinone skeleton such as anthraquinone-1-sulfonic acid, anthraquinone-2-sulfonic acid, and anthraquinone-2-carboxylic acid, and derivatives of these can be used as the compound having the quinone skeleton. Furthermore, one or more kinds of other compounds that act as the electron mediator may be used together with the compound having the quinone skeleton, if necessary.

The cathode in the battery portion only needs to contain catalyst for reducing oxygen in the air, but the cathode preferably contains oxygen reductase. It is more preferable that the oxygen reductase is immobilized on the surface of the cathode.

The oxygen reductase is not particularly limited as long as the oxygen reductase can reduce oxygen. Examples of the oxygen reductase include multi-copper enzymes such as bilirubin oxidase, laccase, and ascorbate oxidase, and analogues of these. Laccase is preferable among these. Further, an electron mediator may be used with these enzymes, and examples of the electron mediator include potassium hexacyanoferrate (II), potassium hexacyanoferrate (III), potassium ferricyanide, and potassium octacyanotungstate.

Materials for forming the anode and cathode are not particularly limited as long as the material has conductivity, but conductive porous materials are preferable. Accordingly, the enzyme can be immobilized more sufficiently. More preferable examples of the conductive porous materials include carbon-based materials such as porous carbon, carbon pellets, carbon felt, carbon paper, or a multilayer body of carbon fiber or carbon particulates. When the lipolysis device according to the present invention includes a buffer layer, described later, between the glycerol introduction portion and the battery portion and the anode is in a dry and depressurized state and partitioning members, which partition the glycerol introduction portion and battery portion from the buffer layer, are broken by external pressure, a compressible and expandable carbon material is preferable as the material for forming the anode.

The materials for forming the anode and the cathode may be the same as or different from each other.

The anode and the cathode may be dry or contain a liquid such as a buffer solution before the lipolysis device is used. When the anode and the cathode are dry, the inside of the system in the battery portion is preferably negative pressure, more preferably a vacuum.

The anode and the cathode preferably further include current collectors.

Any material can be employed for the current collector as long as the current collector is made of the material that can be electrically connected with the outside and the material does not produce electrochemical reactions in the battery portion. Specific examples include metallic materials such as Pt, Ag, Au, Ru, Rh, Os, Nb, Mo, In, Ir, Zn, Mn, Fe, Co, Ti, V, Cr, Pd, Re, Ta, W, Zr, Ge, and Hf; alloys such as alumel, brass, duralumin, bronze, nickelin, platinum-rhodium, permalloy, permendur, nickel silver, and phosphor bronze; conductive polymers such as polyacetylenes; carbon-based materials such as carbon felt, carbon paper, or a multilayer body of carbon fiber or carbon particulates; borides such as $HfB_2$, NbB, $CrB_2$, and $B_4C$; nitrides such as TiN and ZrN; silicides such as $VSi_2$, $NbSi_2$, $MoSi_2$, and $TaSi_2$; and composite materials of these materials.

The battery portion preferably further includes a separator between the anode and the cathode. The separator can be made of any material as long as the material is permeable to protons, but the material is preferably flexible. Specifically, non-woven fabrics, cellophane, perfluorosulfonic acid-based ion exchange membranes, and the like can be used.

In the battery portion, the cathode is preferably covered by a gas diffusion layer through which gas can circulate. A material for forming the gas diffusion layer is not particularly limited, and examples of the material include fluororesins such as polytetrafluoroethylene (PTFE), tetrafluoroethylene-hexafluoropropylene copolymer (FEP), polyvinylidene fluoride (PVdF), tetrafluoroethylene-ethylene copolymer (ETFE), polychlorotrifluoroethylene (PCTFE), and tetrafluoroethylene-perfluoroalkyl vinyl ether copolymer (PFA).

The battery portion is preferably covered by a sealing member that blocks air. When the battery portion is covered by a sealing member, oxygen is supplied to the battery portion by removing the sealing member and the reaction of the battery portion can be started. More preferably, an outer side portion of the gas diffusion layer is covered by the sealing member.

A material for the sealing member is not particularly limited as long as the material can block the air and, for example, polyethylene (PE) and the like are employed.

The lipolysis device may further include a buffer layer containing moisture such as a buffer solution between the glycerol introduction portion and the battery portion. When the anode and cathode in the battery portion, and the protrusions in the glycerol introduction portion are dry, the lipolysis device can be made ready to generate electric power by allowing water in the buffer layer to infiltrate into the anode and cathode in the battery portion and the protrusions in the glycerol introduction portion in use of the lipolysis device.

When the lipolysis device includes the battery portion, as a specific mechanism of the suction mechanism that utilizes a pressure difference in the lipolysis device, an aspect is employed that the insides of the base material, the anode and cathode in the battery portion, and the glycerol introduction portion are in a negative pressure and dry state; a buffer layer containing moisture such as a buffer solution is provided between the base material and the buffer layer; and the base material and the buffer layer, and the battery portion and the buffer layer are partitioned by respective partitioning members which are removable or partitioning members which can be broken by external pressure. In this aspect, if the partitioning members are removed or the partitioning members are broken by external pressure, a liquid in the buffer layer infiltrates into the base material, glycerol introduction portion, and battery portion and water evaporates from the surface of the battery portion. As a result, the pressure in the battery portion drops below the pressure in the glycerol introduction portion and the body fluid in a living body, and this pressure difference allows glycerol in the living body to be sucked through the glycerol introduction portion into the battery portion.

When the partitioning members are removed from the device in use of the lipolysis device having the buffer layer, the material of the partitioning member is not particularly limited as long as the material is a waterproof material and specific examples of the material include polyethylene terephthalate (PET) and polyvinyl chloride (PVC) film.

In the configuration that the partitioning members are broken by external pressure in use of the lipolysis device, examples of a material of the partitioning member include thin-film PVDC, polyethylene, and urethane foam with hydrophobic coated surfaces. Compressible and expandable materials are preferable and urethane foam with hydrophobic coated surfaces are more preferable.

A lipolysis oxidation portion device according to the present invention only needs to contain the base material, the glycerol introduction portion, and the glycerol oxidation portion, but the glycerol oxidation portion device may include other members. Other members are not particularly limited as long as the members do not impair the functionality of the lipolysis device of the present invention. Examples of other members include members that discharges products generated by oxidation of glycerol and/or battery reaction to the outside of the lipolysis device or into a living body; auxiliary members for immobilization such as belts and bandages; and water absorbent polymers.

The lipolysis device according to the present invention consumes fat in subcutaneous tissue of an applied area and therefore, a slimming effect on a desired part of a body can be expected by applying the lipolysis device to the part.

The lipolysis device according to the present invention can be used in an attached manner to a living body and can be used as a patch device such as a slimming patch or a partially-slimming patch.

Electric power obtained by the lipolysis device according to the present invention can be used for various electrical devices. Examples of electrical devices include digital devices having a short-range wireless communication function such as Bluetooth (registered trademark), such as a portable information terminal, a wearable device, a music player, and a digital camera; and implantable medical devices such as artificial organs such as artificial hearts, cardiac pacemakers, insulin and other drug injectors, or in-body monitoring devices such as blood glucose level measuring devices.

In addition, electric power obtained by the lipolysis device can also be converted into vibration energy using an actuator element, and the vibration can be transmitted to the protrusions to promote lipolysis.

Further, the lipolysis device according to the present invention can be connected to a light emitting diode, and consumption of fat by the lipolysis device can be visually notified to a user of the lipolysis device by lighting the light emitting diode.

[Lipolysis Method]

The present invention is a lipolysis method for decomposing fat in a living body and is also a lipolysis method that includes: a lipolysis process for pricking a living body with protrusions, which contain lipolytic enzyme or a peptide compound having equivalent activity to that of the lipolytic enzyme, so as to decompose fat in the living body and obtain glycerol; and an oxidizing process for oxidizing the glycerol, which is obtained in the lipolysis process, by glycerol oxidase in a glycerol oxidation portion.

The lipolysis method according to the present invention is not particularly limited as long as the lipolysis method includes the lipolysis process and the oxidizing process, but the lipolysis method is preferably conducted by using the lipolysis device according to the present invention.

[Electric Power Generation Method]

The present invention is an electric power generation method for generating electric power by using fat in a living body as fuel and is also an electric power generation method that includes: a lipolysis process for pricking a living body with protrusions, which contain lipolytic enzyme or a peptide compound having equivalent activity to that of the lipolytic enzyme, so as to decompose fat in the living body and obtain glycerol; and an oxidizing-reducing process for oxidizing the glycerol, which is obtained in the lipolysis process, in an anode containing glycerol oxidase and for reducing oxygen in the air in a cathode.

The electric power generation method according to the present invention is not particularly limited as long as the electric power generation method includes the lipolysis process and the oxidizing-reducing process, but the electric power generation method is preferably conducted by using the lipolysis device according to the present invention.

Embodiments according to the present invention will now be described below with reference to the accompanying drawings. In all the drawings of the embodiments, the same or corresponding components are given the same reference characters.

FIG. 1 is a diagram illustrating an example of a lipolysis device, which is in use, according to the present invention. This lipolysis device 1 includes a battery portion 2 including a glycerol oxidation portion 6, a glycerol introduction portion 3, and a base material 4. The glycerol introduction portion 3 including protrusions 5 is provided on a surface of the base material 4. When a user presses the surface of the glycerol introduction portion 3 with the protrusions 5 against the user's skin, the protrusions 5 are inserted in the skin.

FIG. 2 is a schematic sectional view of a lipolysis device and skin tissue when the lipolysis device according to the present invention is used.

This lipolysis device 1 includes the battery portion 2 and the glycerol introduction portion 3. The glycerol introduction portion 3 composed of the protrusions 5 is provided on the surface of the base material 4, and the battery portion 2 is provided on a surface, which is an opposite surface to the surface having the protrusions 5, of the base material 4. In the battery portion 2, an anode (glycerol oxidation portion) 6 is arranged so as to be in contact with the base material 4, and a separator 8 and a cathode 7 are laminated on the anode 6 in this order. The anode 6 and the cathode 7 are connected with each other by an external circuit 9. The protrusions 5 are inserted in a skin and lipolytic enzyme 10 contained in the protrusions 5 diffuses into skin tissue 14. The lipolytic enzyme 10 reaches fat cells 15 by the diffusion and decomposes fat. When glycerol 13 generated by the fat decomposition reaches the anode 6 through the protrusions 5, the glycerol 13 is oxidized by glycerol oxidase 11 contained in the anode 6. This generates electrons and protons. The electrons and protons transfer to the cathode 7 via the external circuit 9 and the separator 8 and oxygen is reduced by oxygen reductase 12 in the cathode 7, thus generating electric energy and providing a function as a battery.

Figure 3A:
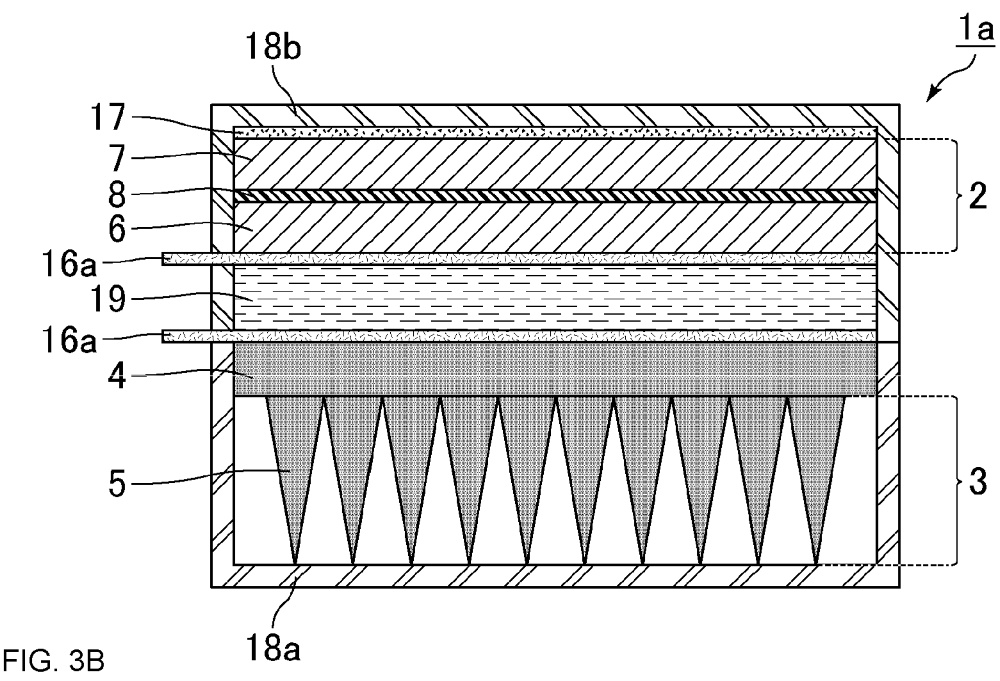
FIG. 3A is a schematic view of a lipolysis device according to a first embodiment of the present invention.

FIG. 3A is a schematic view of a lipolysis device according to a first embodiment of the present invention.

This lipolysis device 1*a* according to the first embodiment includes the battery portion 2 and the glycerol introduction portion 3, and a buffer layer 19 is provided between the battery portion 2 and the glycerol introduction portion 3. In the glycerol introduction portion 3, the protrusions 5 are provided on the surface of the base material 4 and an adhesive layer is provided on a portion, on which the protrusions are not provided, of the surface of the base material 4 on the side having the protrusions 5. The glycerol introduction portion 3 is covered by a sealing member 18*a* so that surfaces of the protrusions 5 are covered.

The base material 4 on the glycerol introduction portion 3 and the buffer layer 19 are partitioned by a partitioning member 16*a*, and the buffer layer 19 and the anode 6 in the battery portion 2 are partitioned by another partitioning member 16*a*. The separator 8, the cathode 7, and a gas diffusion layer 17, which is made of a PTFE film, are laminated on the anode 6 in this order, and the surface of the battery portion 2 is covered by a sealing member 18*b*.

The anode 6 and cathode 7 in the battery portion 2 and the protrusions 5 in the glycerol introduction portion 3 are in a vacuum (reduced pressure) and dry state.

Figure 3B:
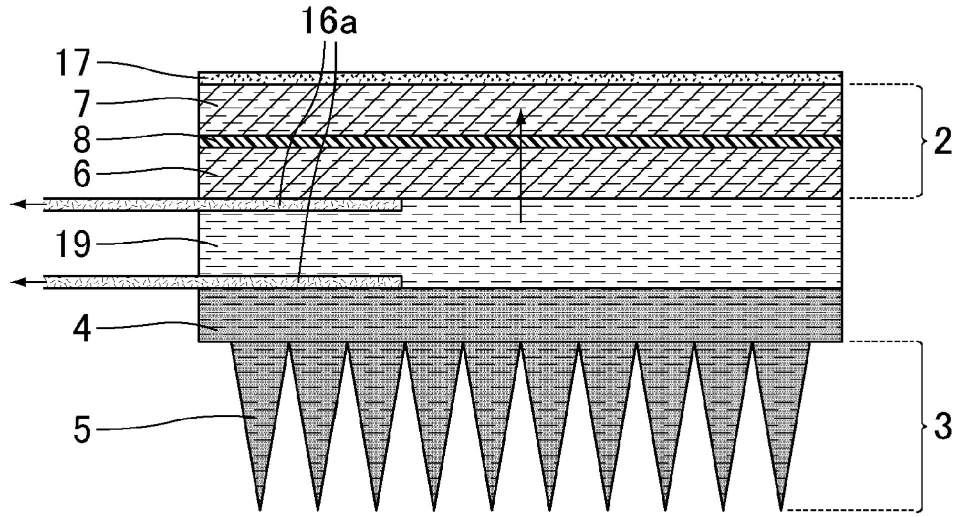
FIG. 3B is a diagram for explaining a glycerol suction mechanism provided in the lipolysis device according to the first embodiment of the present invention.

FIG. 3B is a diagram for explaining a glycerol suction mechanism provided in the lipolysis device according to the first embodiment of the present invention.

By removing the partitioning members 16*a* in the first embodiment, a buffer solution of the buffer layer 19 infiltrates into the anode 6, the cathode 7, and the protrusions 5. The protrusions 5 are exposed by removing the sealing member 18*a* and inserted in a skin. Accordingly, the buffer solution in the protrusions 5 is brought into contact with interstitial fluid in skin tissue. When the gas diffusion layer 17 is exposed to the atmosphere by removing the sealing member 18*b*, moisture infiltrated in the anode 6 and cathode 7 evaporates through the gas diffusion layer 17. Accordingly, body fluid in the skin tissue containing glycerol is sucked up to the anode 6 through the protrusions 5.

Figure 4A:
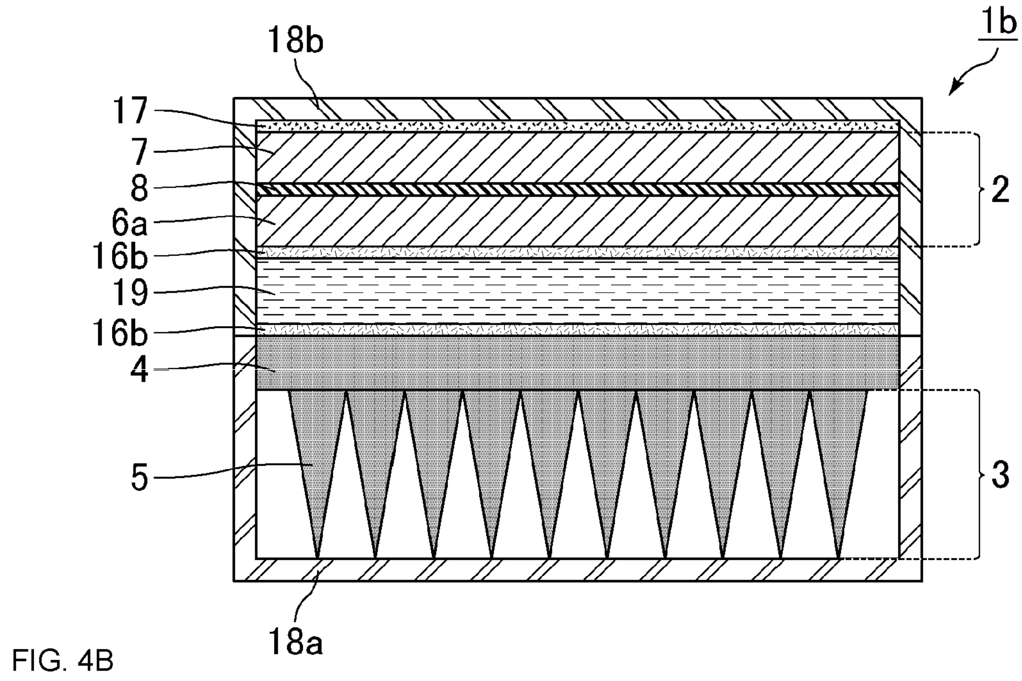
FIG. 4A is a schematic view of a lipolysis device according to a second embodiment of the present invention.

FIG. 4A is a schematic view of a lipolysis device according to a second embodiment of the present invention.

This lipolysis device 1*b* according to the second embodiment includes the battery portion 2 and the glycerol introduction portion 3, and the buffer layer 19 is provided between the battery portion 2 and the glycerol introduction portion 3. In the glycerol introduction portion 3, the protrusions 5 are provided on the surface of the base material 4 and an adhesive layer is provided on a portion, on which the protrusions are not provided, of the surface of the base material 4 on the side having the protrusions 5. The glycerol introduction portion 3 is covered by the sealing member 18*a* so that surfaces of the protrusions 5 are covered.

The base material 4 on the glycerol introduction portion 3 and the buffer layer 19 are partitioned by a partitioning member 16*b*, and the buffer layer 19 and an anode 6*a* in the battery portion 2 are partitioned by another partitioning member 16*b*. The separator 8, the cathode 7, and the gas diffusion layer 17 are laminated on the anode 6*a* in this order, and the surface of the battery portion 2 is covered by the sealing member 18*b*.

The anode 6*a* and cathode 7 in the battery portion 2 and the protrusions 5 in the glycerol introduction portion 3 are in a vacuum (reduced pressure) and dry state.

The anode 6*a* is made of a compressible and expandable carbon material, the partitioning member 16*b* is made of a compressible and expandable material, and the gas diffusion layer 17 is made of a PTFE film.

Figure 4B:
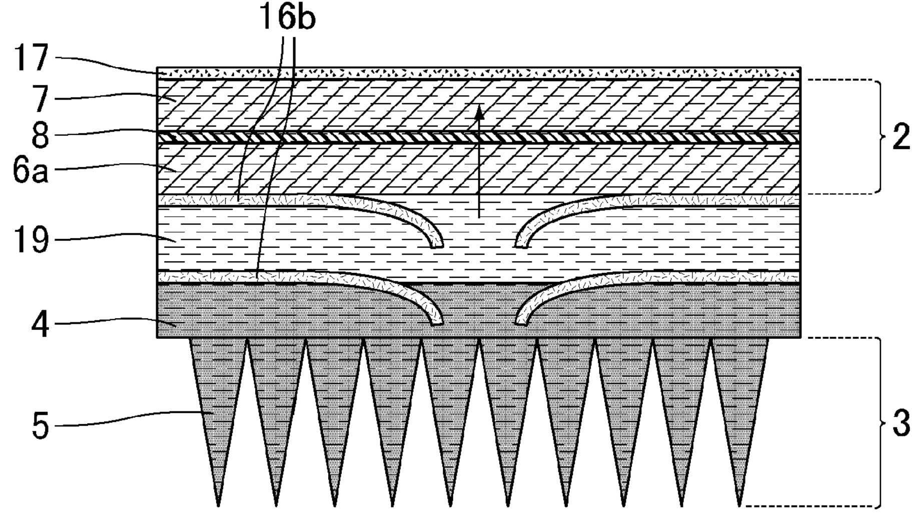
FIG. 4B is a diagram for explaining a glycerol suction mechanism provided in the lipolysis device according to the second embodiment of the present invention.

FIG. 4B is a diagram for explaining a glycerol suction mechanism provided in the lipolysis device according to the second embodiment of the present invention.

The protrusions 5 are exposed by removing the sealing member 18*a* according to the second embodiment and the lipolysis device 1*b* is pressed against a skin so as to insert the protrusions 5 in the skin. The partitioning members 16*b* are broken by pressure for pressing the lipolysis device 1*b* against the skin, and the buffer solution of the buffer layer 19 infiltrates into the anode 6*a*, the cathode 7, and the protrusions 5. Accordingly, the buffer solution in the protrusions 5 is brought into contact with interstitial fluid in skin tissue. When the gas diffusion layer 17 is exposed to the atmosphere by removing the sealing member 18*b*, moisture infiltrated in the anode 6*a* and cathode 7 evaporates through the gas diffusion layer 17. Accordingly, body fluid in the skin tissue containing glycerol is sucked up to the anode 6*a* through the protrusions 5. The anode 6*a* and the partitioning members 16*b* are made of the compressible and expandable material. Therefore, a restoring force of the partitioning members 16*b* and the anode 6*a* generated by the breaking of the decompression state caused by the breaking of the partitioning members 16*b* also increases a speed of sucking the body fluid in the skin tissue up to the anode 6*a*.

Figure 5:
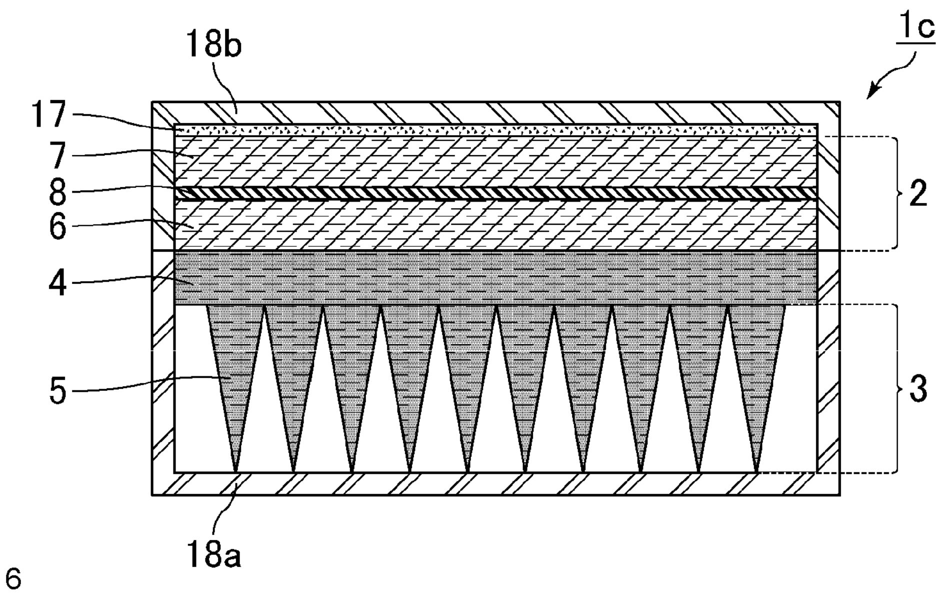
FIG. 5 is a schematic view of a lipolysis device according to a third embodiment of the present invention.

FIG. 5 is a schematic view of a lipolysis device according to a third embodiment of the present invention.

This lipolysis device 1*c* according to the third embodiment includes the battery portion 2 and the glycerol introduction portion 3. In the glycerol introduction portion 3, the protrusions 5 are provided on the surface of the base material 4 and an adhesive layer is provided on a portion, on which the protrusions are not provided, of the surface of the base material 4 on the side having the protrusions 5. The glycerol introduction portion 3 is covered by the sealing member 18*a* so that the surfaces of the protrusions 5 are covered. In the battery portion 2, the anode 6 is arranged so as to be in contact with the base material 4 on the glycerol introduction portion 3, and the separator 8, the cathode 7, and the gas diffusion layer 17, which is made of a PTFE film, are laminated on the anode 6 in this order. The surface of the battery portion 2 is covered by the sealing member 18*b*.

The anode 6 and cathode 7 in the battery portion 2 and the protrusions 5 in the glycerol introduction portion 3 are wetted by a buffer solution. The protrusions 5 are exposed by removing the sealing member 18*a* and inserted in a skin. Accordingly, the buffer solution in the protrusions 5 is brought into contact with interstitial fluid in skin tissue. When the gas diffusion layer 17 is exposed to the atmosphere by removing the sealing member 18*b*, moisture in the anode 6 and cathode 7 evaporates through the gas diffusion layer 17. Accordingly, body fluid in the skin tissue containing glycerol is sucked up to the anode 6 through the protrusions 5.

Figure 6:
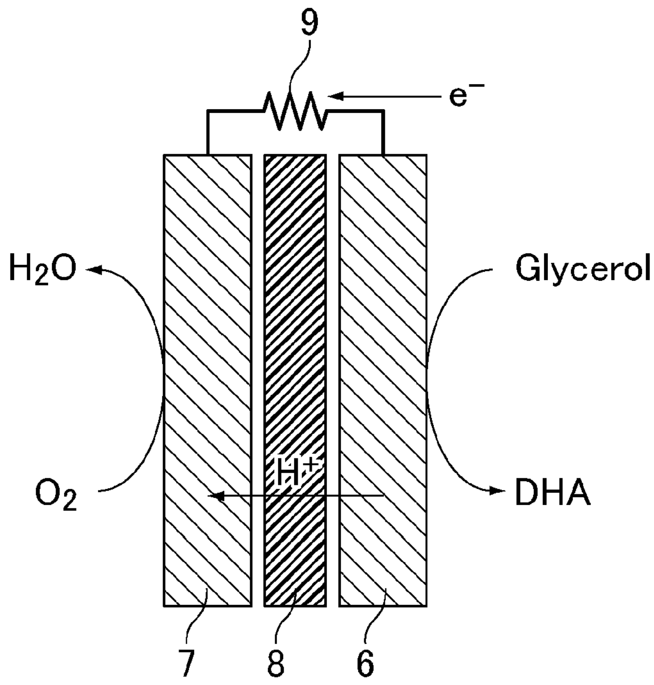
FIG. 6 is a diagram schematically illustrating a principle of electric power generation in a battery portion of the lipolysis device according to the present invention.

FIG. 6 is a diagram schematically illustrating a principle of electric power generation in a battery portion of the lipolysis device according to the present invention.

The separator 8 is arranged between the anode 6 and the cathode 7, and the anode 6 and the cathode 7 are connected by the external circuit 9.

When glycerol dehydrogenase is immobilized as the glycerol oxidase on the surface of the anode 6, glycerol is dehydrogenated by glycerol dehydrogenase to extract electrons ($e^-$) and produce dihydroxyacetone (DHA). Further, at the cathode 7, oxygen (02) in the air is reduced by protons ($H^-$) transferred from the anode 6 through the separator 8 and electrons ($e^-$) sent through the external circuit 9, producing water ($H_2O$). These reactions occur simultaneously, generating electrical energy between electrodes.

EXAMPLES

The present invention will be described in more detail with reference to examples below, but the present invention is not limited only to these examples.

Manufacturing Example 1: Formation of Protrusions (Microneedle Array) in Glycerol Introduction Portion A resin mold was formed by injection molding into a microneedle array master mold (master mold formed of 100 conical needles of φ: 0.5 mm, h: 0.65 mm). Polylactic acid was injection-molded into the resin mold to make porous microneedle arrays.

Protrusions of the obtained microneedle arrays were treated with plasma to make the protrusions hydrophilic.

Using a contact angle meter (Model CA-X, Kyowa Interface Science Co., Ltd.), the contact angle (θ) with water on the surface of the protrusions was measured 10 seconds after 0.3 μl of distilled water was dropped onto the protrusions of the resulting hydrophilic microneedle arrays. A contact angle with water on the surface of the protrusions was 35°.

The protrusions of the microneedle arrays were immersed in an aqueous solution containing lipase with pH adjusted from 6 to 9, and then dried at 30° C.

Accordingly, the lipase was immobilized on the protrusions of the porous microneedle arrays by ionic bonding between the carboxyl group of the polylactic acid and the amino group of the lipase.

Example 1: Manufacturing of Lipolysis Device

A battery portion was installed so that an anode was crimped onto the back of the microneedle arrays obtained in Manufacturing example 1. In the battery portion, the anode with glycerol dehydrogenase immobilized on its surface and a cathode with laccase enzyme immobilized on its surface have liquid junction through the separator. Carbon fiber electrodes were used for the anode and cathode. Nonwoven fabric made of PTFE was used for the separator. A coil (inductor) in a circuit that increases a voltage was used as an external circuit for the battery portion.

The microneedle arrays obtained in Manufacturing example 1 and the lipolysis device obtained in Example 1 were used to evaluate the following physical properties.

1. Evaluation of Enzymatic Activity of Lipolytic Enzyme Immobilized on Protrusion Animal meat containing fat was pricked with the protrusions of the microneedle arrays obtained in Manufacturing example 1 and Glycerol Assay Kit manufactured by Cayman Chemical was used to check glycerol generation.

2. Evaluation of Electric Power Generation by Lipolysis Device

A light emitting diode was connected to the lipolysis device obtained in Example 1, and the diode lit up when the protrusions of the lipolysis device were invaded in a skin.

REFERENCE SIGNS LIST

1, 1*a*, 1*b*, 1*c* lipolysis device
2 battery portion
3 glycerol introduction portion
4 base material
5 protrusion
6, 6*a* anode (glycerol oxidation portion)
7 cathode
8 separator
9 external circuit
10 lipolytic enzyme
11 glycerol oxidase
12 oxygen reductase
13 glycerol
14 skin tissue
15 fat cell
16*a*, 16*b* partitioning member
17 gas diffusion layer
18*a*, 18*b* sealing member
19 buffer layer

The invention claimed is:

1. A lipolysis device comprising:

a base material having a first surface and a second surface opposite the first surface;

a glycerol introduction portion on the first surface of the base material, the glycerol introduction portion having a protrusion containing a lipolytic enzyme or a peptide compound having equivalent activity to that of the lipolytic enzyme; and a glycerol oxidation portion on the second surface of the base material, the glycerol oxidation portion containing glycerol oxidase that oxidizes glycerol introduced from the glycerol introduction portion.

2. The lipolysis device according to claim 1, further comprising:

a battery that includes an anode and a cathode, wherein the anode is the glycerol oxidation portion.

3. The lipolysis device according to claim 2, wherein the cathode contains oxygen reductase and reduces oxygen in air.

4. The lipolysis device according to claim 2, wherein the anode contains a coenzyme oxidase and an electron mediator.

5. The lipolysis device according to claim 1, wherein a contact angle with water on a surface of the protrusion is 60° or smaller.

6. The lipolysis device according to claim 1, wherein a length of the protrusion is from 100 μm to 3000 μm inclusive.

7. The lipolysis device according to claim 1, wherein the protrusion is a porous body.

8. The lipolysis device according to claim 7, wherein D50 of the protrusion in pore diameter distribution is from 0.05 μm to 10 μm inclusive.

9. The lipolysis device according to claim 1, wherein the protrusion is made of a biodegradable material.

10. The lipolysis device according to claim 1, wherein the lipolytic enzyme or the peptide compound having equivalent activity to that of the lipolytic enzyme is bound to or adsorbed on the protrusion.

11. The lipolysis device according to claim 1, wherein the protrusion contains the lipolytic enzyme, and an average molecular weight of the lipolytic enzyme is from 2000 to 100000 inclusive.

12. The lipolysis device according to claim 1, wherein the lipolytic enzyme or the peptide compound having equivalent activity to that of the lipolytic enzyme is a lipase or a peptide compound having equivalent activity to that of the lipase.

13. The lipolysis device according to claim 1, further comprising:

a suction mechanism constructed to suck the glycerol from the glycerol introduction portion into the glycerol oxidation portion.

14. The lipolysis device according to claim 13, wherein the suction mechanism constructed to operate based on a pressure difference in the lipolysis device.

15. The lipolysis device according to claim 13, wherein the suction mechanism is constructed to utilize a capillary force.

16. The lipolysis device according to claim 1, wherein the glycerol oxidase is at least one selected from a group consisting of glycerol dehydrogenase, alcohol dehydrogenase, glycerol oxidase, and analogues thereof.

17. The lipolysis device according to claim 1, wherein a surface of the protrusion is hydrophilic.

18. A lipolysis method for decomposing fat in a living body, the lipolysis method comprising:

using a lipolysis device that includes a base material having a first surface and a second surface opposite the first surface; a glycerol introduction portion on the first surface of the base material, the glycerol introduction portion having a protrusion containing a lipolytic enzyme or a peptide compound having equivalent activity to that of the lipolytic enzyme; and a glycerol oxidation portion on the second surface of the base material, the glycerol oxidation portion containing glycerol oxidase to prick the living body with the protrusion containing the lipolytic enzyme or the peptide compound having equivalent activity to that of the lipolytic enzyme so as to decompose fat in the living body and obtain glycerol; and oxidizing the glycerol with glycerol oxidase in the glycerol oxidation portion.

19. An electric power generation method for generating electric power using fat in a living body as fuel, the electric power generation method comprising:

pricking the living body with a protrusion, the protrusion containing lipolytic enzyme or a peptide compound having equivalent activity to that of the lipolytic enzyme so as to decompose fat in the living body and obtain glycerol; and oxidizing the glycerol in an anode containing glycerol oxidase, and reducing oxygen in air in a cathode.

* * * * *